United States Patent
Ishigami et al.

(10) Patent No.: US 11,623,230 B2
(45) Date of Patent: Apr. 11, 2023

(54) VOLTAGE APPLICATION DEVICE AND DISCHARGE DEVICE

(71) Applicant: Panasonic Intellectual Property Management Co., Ltd., Osaka (JP)

(72) Inventors: Yohei Ishigami, Osaka (JP); Jumpei Oe, Shiga (JP); Yukari Nakano, Shiga (JP); Takafumi Omori, Shiga (JP); Tetsunori Aono, Hyogo (JP); Kana Shimizu, Shiga (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 10 days.

(21) Appl. No.: 16/641,992

(22) PCT Filed: Jul. 24, 2018

(86) PCT No.: PCT/JP2018/027587
§ 371 (c)(1),
(2) Date: Feb. 25, 2020

(87) PCT Pub. No.: WO2019/044272
PCT Pub. Date: Mar. 7, 2019

(65) Prior Publication Data
US 2020/0353488 A1    Nov. 12, 2020

(30) Foreign Application Priority Data

Aug. 31, 2017    (JP) .............................. JP2017-168043

(51) Int. Cl.
*B05B 5/00*    (2006.01)
*B05B 5/025*    (2006.01)
*B05B 5/057*    (2006.01)

(52) U.S. Cl.
CPC .............. *B05B 5/006* (2013.01); *B05B 5/007* (2013.01); *B05B 5/0255* (2013.01); *B05B 5/057* (2013.01)

(58) Field of Classification Search
CPC ....... B05B 5/006; B05B 5/007; B05B 5/0255; B05B 5/057; B05B 5/005; B05B 5/10; B05B 5/025; B05B 5/0535
(Continued)

(56) References Cited

U.S. PATENT DOCUMENTS 3,725,738 A * 4/1973 Sokolsky .................. B05B 5/10
361/235
6,439,474 B2 * 8/2002 Denen ....................... A61L 9/14
239/102.2
(Continued)

FOREIGN PATENT DOCUMENTS

JP    H0825723 B2 *  3/1996 ............. C01B 13/11
JP    2009-72718 A     4/2009
(Continued)

OTHER PUBLICATIONS

Machine Translation of JP-2013075266-A Description, Jul. 27, 2021, Google Patents, 10 Pages (Year: 2021).*
(Continued)

*Primary Examiner* — Tuongminh N Pham
*Assistant Examiner* — Kevin Edward Schwartz
(74) *Attorney, Agent, or Firm* — McDermott Will & Emery LLP

(57) ABSTRACT

Voltage application device includes voltage application circuit. Voltage application circuit applies a voltage to load including discharge electrode that holds liquid, voltage application circuit generating discharge in discharge electrode. During a drive period, voltage application circuit periodically changes a magnitude of the voltage applied to
(Continued)

load at a drive frequency within a predetermined range including a resonance frequency of liquid, voltage application circuit mechanically vibrating liquid.

12 Claims, 5 Drawing Sheets

(58) Field of Classification Search
USPC .......................................................... 239/69
See application file for complete search history.

(56) References Cited

U.S. PATENT DOCUMENTS

| | | | |
|---|---|---|---|
| 7,861,954 B2* | 1/2011 | Akisada | B05B 5/057 239/690 |
| 8,056,839 B2* | 11/2011 | Uratani | B05B 5/057 239/691 |
| 2012/0126041 A1 | 5/2012 | Nunomura et al. | |
| 2014/0209710 A1* | 7/2014 | Komura | B05B 5/0533 239/690 |
| 2016/0031708 A1* | 2/2016 | Machi | H01T 23/00 422/186.2 |

FOREIGN PATENT DOCUMENTS

| | | |
|---|---|---|
| JP | 2011-67738 A | 4/2011 |
| JP | 2013-75266 A | 4/2013 |
| JP | 2013-116444 A | 6/2013 |

OTHER PUBLICATIONS

Machine Translation of JP-2013-116444-A Description, Jul. 28, 2021, Google Patents, 8 Pages (Year: 2021).*
Machine Translation of JP-H0825723-B2 Description, Dec. 2, 2021, Google Patents, 10 Pages (Year: 2021).*
International Search Report issued in corresponding International Patent Application No. PCT/JP2018/027587, dated Sep. 18, 2018, with English translation.

* cited by examiner

VOLTAGE APPLICATION DEVICE AND DISCHARGE DEVICE

CROSS-REFERENCE OF RELATED APPLICATIONS

This application is a U.S. national stage application of U.S.C. § 371 of International Patent Application No. PCT/JP2018/027587 filed on Jul. 24, 2018, which claims the benefit of foreign priority of Japanese Patent Application No. 2017-168043 filed on Aug. 31, 2017, the contents all of which are incorporated herein by reference.

TECHNICAL FIELD

The present disclosure generally relates to a voltage application device and a discharge device, and more specifically, a voltage application device and a discharge device that apply voltage to a load including a discharge electrode to generate discharge.

BACKGROUND ART

Conventionally, a discharge device has been provided that includes a discharge electrode and a voltage application circuit (a power supply unit) (see, for example, PTL 1).

This type of discharge device causes a voltage application circuit to apply voltage to a discharge electrode, and generates corona discharge. In a case where liquid has been supplied to the discharge electrode, electrostatic atomization is performed at the time of discharge, and charged fine particle liquid that contains radicals serving as an active ingredient can be generated. The charged fine particle liquid containing radicals exhibits effects such as sterile filtration or odor removal.

CITATION LIST

Patent Literature

PTL 1: Unexamined Japanese Patent Publication No. 2011-67738

SUMMARY OF THE INVENTION

However, in the discharge device described in PTL 1, there is a possibility that discharge will become unstable, for example, due to a variation in a magnitude of a voltage applied to the discharge electrode, a variation in a shape of the discharge electrode, a variation in an amount (a volume) of liquid supplied to the discharge electrode, or the like.

The present disclosure provides a voltage application device and a discharge device that are capable of more stably generating discharge.

A voltage application device in one aspect of the present disclosure includes a voltage application circuit. The voltage application circuit applies a voltage to a load including a discharge electrode that holds liquid, and generates discharge in the discharge electrode. During a drive period, the voltage application circuit periodically changes a magnitude of the voltage applied to the load at a drive frequency within a predetermined range including a resonance frequency of the liquid, and mechanically vibrates the liquid.

A discharge device in one aspect of the present disclosure includes the voltage application device and the discharge electrode.

The present disclosure has an advantage by which discharge can be generated more stably.

DESCRIPTION OF EMBODIMENTS

First Exemplary Embodiment (1) Outline

Figure 1:
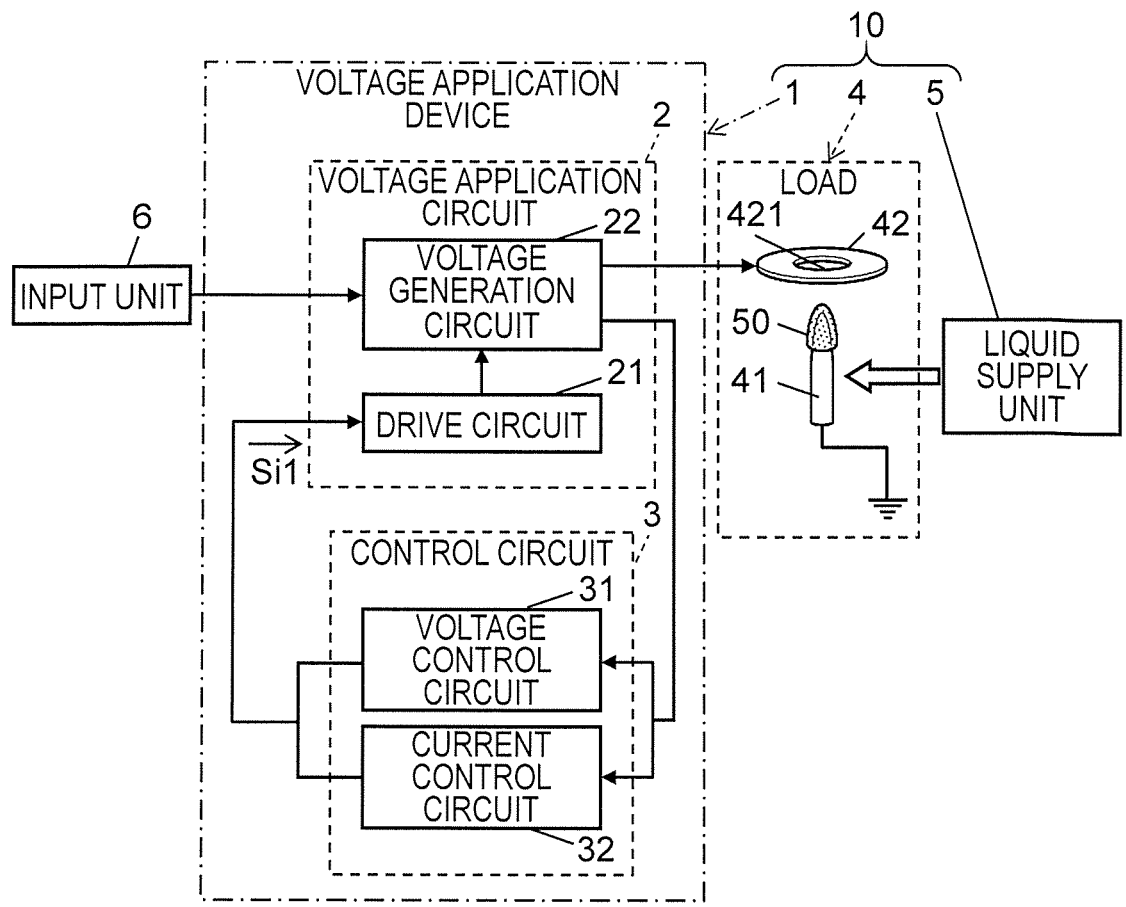
FIG. 1 is a block diagram of a discharge device according to a first exemplary embodiment.

As illustrated in FIG. 1, voltage application device 1 according to the present exemplary embodiment includes voltage application circuit 2 and control circuit 3. Voltage application device 1 is a device that applies a voltage to load 4 including discharge electrode 41 to cause discharge electrode 41 to generate discharge.

In addition, discharge device 10 according to the present exemplary embodiment includes voltage application device 1, load 4, and liquid supply unit 5, as illustrated in FIG. 1. Load 4 includes discharge electrode 41 and counter electrode 42. Counter electrode 42 is an electrode that is disposed so as to face discharge electrode 41 via a gap. Load 4 causes discharge to occur between discharge electrode 41 and counter electrode 42 due to application of voltage between discharge electrode 41 and counter electrode 42. Liquid supply unit 5 has a function of supplying liquid 50 to discharge electrode 41. Stated another way, discharge device 10 includes voltage application circuit 2, control circuit 3, liquid supply unit 5, discharge electrode 41, and counter electrode 42 as components. It is sufficient if discharge device 10 includes voltage application device 1 and discharge electrode 41 as minimum components, and each of counter electrode 42 and liquid supply unit 5 may be omitted from components of discharge device 10.

Discharge device 10 according to the present exemplary embodiment applies a voltage from voltage application circuit 2 to load 4 including discharge electrode 41 in a state where liquid 50 is held in discharge electrode 41, for example, by liquid 50 adhering to a surface of discharge electrode 41. This causes discharge to occur at least in discharge electrode 41, and liquid 50 held in discharge electrode 41 is electrostatically atomized due to discharge. Stated another way, discharge device 10 according to the present exemplary embodiment configures what is called an electrostatic atomization device. In the present disclosure, liquid 50 held in discharge electrode 41, and in other words, liquid 50 serving as a target for electrostatic atomization, is also simply referred to as "liquid 50".

Meanwhile, voltage application circuit 2 mechanically vibrates liquid 50 by periodically changing a magnitude of a voltage to be applied to load 4 (hereinafter, the voltage to be applied to load 4 is also referred to as an "applied voltage") at a drive frequency during a drive period. The drive frequency is a frequency that is set within a predetermined range including a resonance frequency of liquid 50. The "drive period" in the present disclosure is a period during which voltage application device 1 is driven to cause discharge electrode 41 to generate discharge. In the present exemplary embodiment, voltage application circuit 2 is controlled by control circuit 3, and therefore control circuit 3 performs the adjustment of the magnitude of the applied voltage, as described above.

Stated another way, during the drive period, voltage application circuit 2 does not maintain the magnitude of a voltage to be applied to load 4 including discharge electrode 41 at a fixed value, but periodically changes the magnitude of the voltage at a drive frequency within a predetermined range including the resonance frequency of liquid 50. By doing this, a magnitude of electric energy that acts on liquid 50 held in discharge electrode 41 periodically changes at the drive frequency, and consequently liquid 50 held in discharge electrode 41 mechanically vibrates at the drive frequency. Here, the drive frequency serving as a frequency of a change in the applied voltage is set to fall within a predetermined range including the resonance frequency (a natural frequency) of liquid 50 held in discharge electrode 41, and in other words, to have a value near the resonance frequency of liquid 50. Therefore, an amplitude of mechanical vibration of liquid 50 due to a change in the magnitude of the applied voltage becomes relatively large.

Figure 2A:
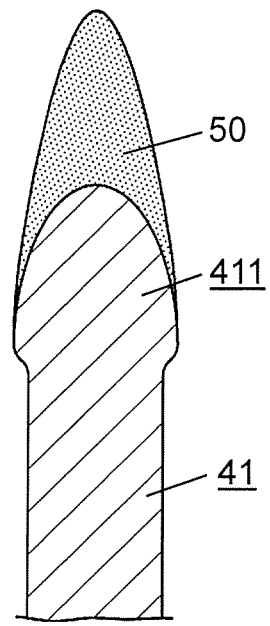
FIG. 2A is a schematic diagram illustrating a state where liquid held in a discharge electrode has expanded in the discharge device according to the first exemplary embodiment.

Details will be described later, but voltage (the applied voltage) is applied to load 4, and therefore liquid 50 held in discharge electrode 41 receives a force caused by an electric field, and has a shape of a cone called a Taylor cone, as illustrated in FIG. 2A. The electric field is concentrated on a distal end serving as a vertex of the Taylor cone, so that discharge occurs. At this time, as the distal end of the Taylor cone becomes more sharply pointed, and in other words, as a vertex angle of the cone becomes smaller, a field intensity required for dielectric breakdown is reduced, and discharge occurs more easily. Liquid 50 held in discharge electrode 41 is alternately transformed between a shape illustrated in FIG. 2A and a shape illustrated in FIG. 2B according to the mechanical vibration. As a result, the Taylor cone described above is periodically formed, and therefore discharge intermittently occurs in accordance with a timing at which a Taylor cone illustrated in FIG. 2A is formed.

As a result, discharge device 10 according to the present exemplary embodiment repeats a phenomenon in which, when corona discharge develops into dielectric breakdown, a relatively large discharge current instantaneously flows, immediately after this, the applied voltage decreases and the discharge current is interrupted, and the applied voltage increases again and dielectric breakdown occurs. Hereinafter, discharge having a form of intermittently repeating a phenomenon in which corona discharge develops into dielectric breakdown, as described above, is referred to as "leader discharge". Stated another way, in discharge device 10, a discharge path is intermittently formed around discharge electrode 41 due to leader discharge, and a pulse-like discharge current is repeatedly generated. Details of leader discharge will be described in the section "(2.2) Leader discharge".

In leader discharge, as described above, radicals are generated at energy that is larger than energy in corona discharge, and a large number of radicals are generated that corresponds to approximately two to ten times the number of radicals generated in corona discharge. The radicals generated as described above become a base of the exhibition of advantageous effects including sterile filtration, odor removal, moisture keeping, freshness keeping, and virus inactivation in various situations. Here, when radicals are generated due to leader discharge, ozone is also generated. In leader discharge, a certain number of radicals are generated that corresponds to approximately two to ten times the number of radicals generated in corona discharge, but a generation amount of ozone is nearly equal to a generation amount of ozone in the case of corona discharge. Accordingly, according to voltage application device 1 and discharge device 10 including voltage application device 1 according to the present exemplary embodiment, an increase in a generation amount of ozone can be suppressed while the number of generated radicals is increased.

In discharge device 10 according to the present exemplary embodiment, liquid 50 vibrates at a relatively large amplitude by mechanically vibrating at a drive frequency near a resonance frequency of liquid 50. Therefore, in liquid 50, a distal end serving as a vertex of a Taylor cone generated when an electric field acts has a more sharply pointed shape in comparison with a case where liquid 50 mechanically vibrates at a frequency away from the resonance frequency of liquid 50. Accordingly, in liquid 50, a field intensity required for dielectric breakdown in a state where the Taylor cone has been formed is reduced, and discharge more easily occurs, in comparison with a case where liquid 50 mechanically vibrates at a frequency away from the resonance frequency of liquid 50. Therefore, for example, even when there is a variation in a magnitude of a voltage applied from voltage application circuit 2 to load 4, namely, applied voltage, a variation in a shape of discharge electrode 41, or a variation in an amount (a volume) of liquid 50 supplied to discharge electrode 41, leader discharge can stably occur. In addition, voltage application circuit 2 can reduce a magnitude of a voltage to be applied to load 4 including discharge electrode 41 to a relatively small value. Therefore, a structure around discharge electrode 41 for insulation measures can be simplified, or pressure resistance of parts that are used for voltage application circuit 2 or the like can be reduced.

(2) Details

Voltage application device 1 and discharge device 10 according to the present exemplary embodiment are described below in more detail.

(2.1) Entire configuration

Discharge device 10 according to the present exemplary embodiment includes voltage application circuit 2, control circuit 3, load 4, and liquid supply unit 5, as illustrated in FIG. 1. Load 4 includes discharge electrode 41 and counter electrode 42. Liquid supply unit 5 supplies liquid 50 to discharge electrode 41. In FIG. 1, shapes of discharge electrode 41 and counter electrode 42 are schematically illustrated.

Discharge electrode 41 is an electrode having a bar shape. Discharge electrode 41 includes distal end 411 (see FIGS. 2A and 2B) at one end along a longitudinal axis of discharge electrode 41, and includes base end 412 (see FIG. 3B) at another end along the longitudinal axis (an end on an opposite side of the distal end). Discharge electrode 41 is a needle electrode in which at least distal end 411 has a tapered shape. The "tapered shape" here is not limited to a shape having a sharply pointed distal end, but includes a shape having a roundish distal end, as illustrated in FIG. 2A or the like.

Counter electrode 42 is disposed to face the distal end of discharge electrode 41. Counter electrode 42 has, for example, a plate shape, and counter electrode 42 has an annular shape including opening 421 in a center. Opening 421 penetrates counter electrode 42 along a thickness axis of counter electrode 42. Here, a positional relationship between counter electrode 42 and discharge electrode 41 has been determined in such a way that the thickness axis of counter electrode 42 (a penetration axis of opening 421) matches a longitudinal axis of discharge electrode 41 and the distal end of discharge electrode 41 is located near a center of opening 421 of counter electrode 42. Stated another way, due to at least opening 421 of counter electrode 42, a gap (a space) is secured between counter electrode 42 and discharge electrode 41. In other words, counter electrode 42 is disposed to face discharge electrode 41 via the gap, and counter electrode 42 is electrically insulated against discharge electrode 41.

Figure 3A:
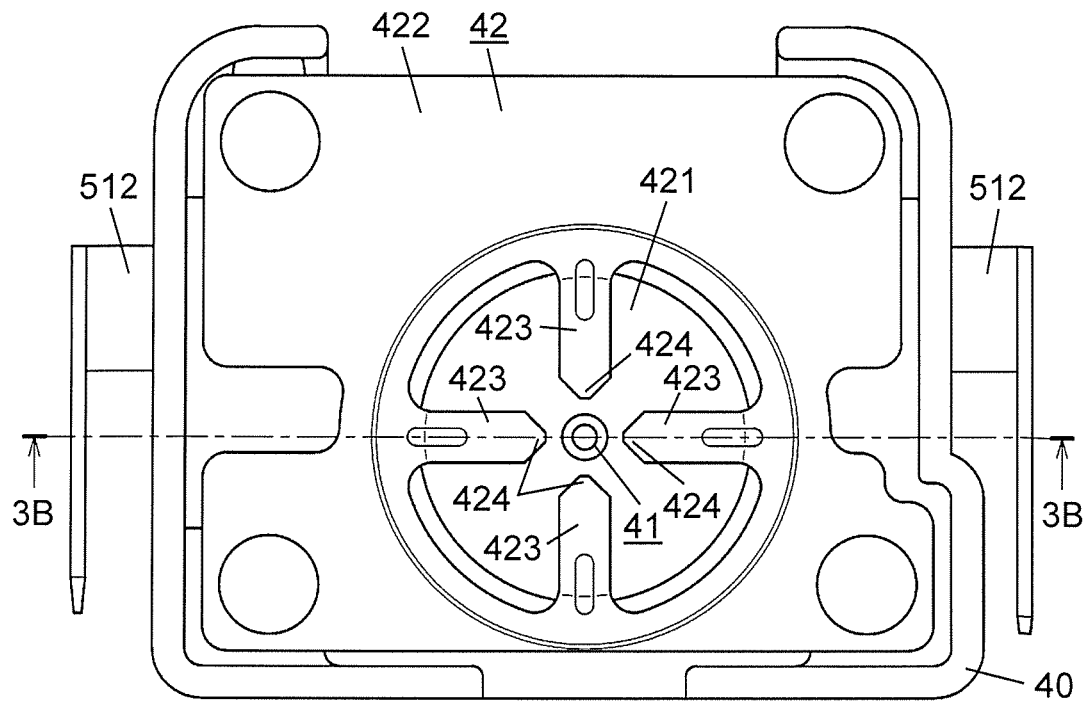
FIG. 3A is a plan view illustrating the discharge electrode and a counter electrode in the discharge device according to the first exemplary embodiment.
Figure 3B:
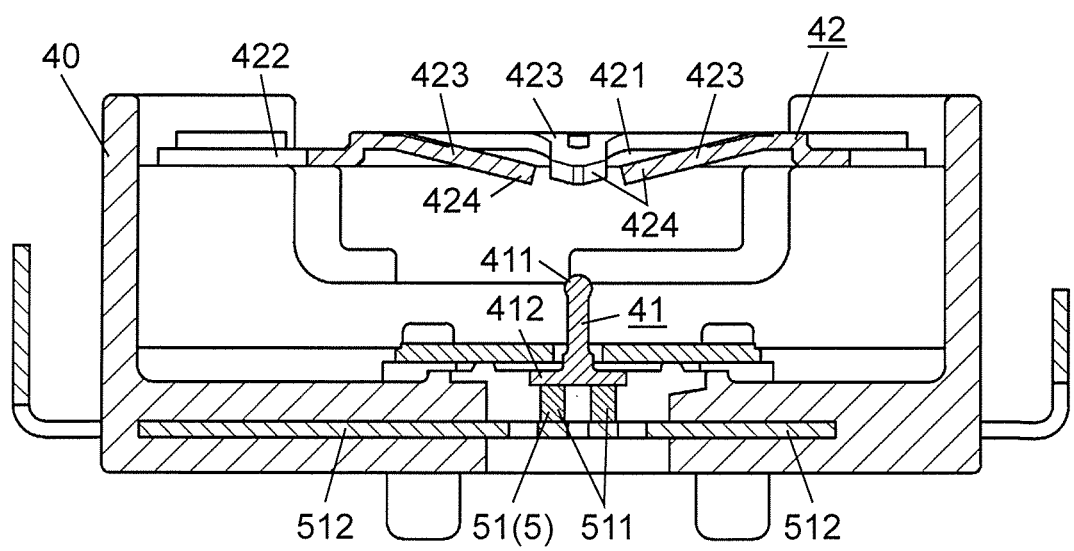
FIG. 3B is a sectional view taken along 3B-3B in FIG. 3A.

More specifically, discharge electrode 41 and counter electrode 42 are formed, as an example, in shapes illustrated in FIGS. 3A and 3B. Stated another way, counter electrode 42 includes support part 422 and four needle-shaped parts 423. Discharge electrode 41 and counter electrode 42 are held in housing 40 that has electric insulation and is made of synthetic resin. Support part 422 has a flat plate shape, and includes opening 421 that is open in a circular shape. Four needle-shaped parts 423 are disposed at equal intervals in a circumference of opening 421. Each of needle-shaped parts 423 protrudes toward the center of opening 421 from an inner circumferential edge of opening 421 in support part 422. Each of needle-shaped parts 423 includes extension part 424 having a tapered shape at a distal end along a longitudinal axis (an end on a side of the center of opening 421). Here, each of needle-shaped parts 423 obliquely protrudes in a direction toward discharge electrode 41 from the inner circumferential edge of opening 421 in such a way that a distance along the longitudinal axis of discharge electrode 41 between each of needle-shaped parts 423 and discharge electrode 41 decreases in a part closer to extension part 424 on a side of a distal end of each of needle-shaped parts 423. By forming each of needle-shaped parts 423 in the shape described above, electric field concentration easily occurs in extension part 424 of each of needle-shaped parts 423. As a result, leader discharge easily and stably occurs between extension 424 of each of needle-shaped parts 423 and distal end 411 of discharge electrode 41.

Liquid supply unit 5 supplies liquid 50 for electrostatic atomization to discharge electrode 41. Liquid supply unit 5 is implemented, as an example, by using cooler 51 that cools down discharge electrode 41 and causes discharge electrode 41 to generate dew condensation water. Specifically, cooler 51 includes, as an example, a pair of Peltier elements 511 and a pair of radiator plates 512, as illustrated in FIG. 3B. The pair of Peltier elements 511 are held in the pair of radiator plates 512. Cooler 51 carries a current to the pair of Peltier elements 511 to cool down discharge electrode 41. Part of each of the pair of radiator plates 512 is embedded into housing 40, so that the pair of radiator plates 512 are held in housing 40. In the pair of radiator plates 512, at least portions that hold Peltier elements 511 are exposed from housing 40.

The pair of Peltier elements 511 are mechanically and electrically connected to base end 412 of discharge electrode 41, for example, by using solder. The pair of Peltier elements 511 are mechanically and electrically connected to the pair of radiator plates 512, for example, by using solder. A current is carried to the pair of Peltier elements 511 via the pair of radiator plates 512 and discharge electrode 41. Accordingly, cooler 51 that configures liquid supply unit 5 cools down an entirety of discharge electrode 41 via base end 412. By doing this, moisture in the air is condensed, and adheres to a surface of discharge electrode 41 as dew condensation water. Stated another way, liquid supply unit 5 is configured to cool down discharge electrode 41 and generate dew condensation water as liquid 50 on the surface of discharge electrode 41. In this configuration, liquid supply unit 5 can supply liquid 50 (dew condensation water) to discharge electrode 41 by utilizing moisture in the air, and therefore discharge electrode 10 does not need to be supplied and be replenished with liquid.

Voltage application circuit 2 includes drive circuit 21 and voltage generation circuit 22, as illustrated in FIG. 1. Drive circuit 21 is a circuit that drives voltage generation circuit 22. Voltage generation circuit 22 is a circuit that receives power supply from input unit 6 and generates a voltage to be applied to load 4 (an applied voltage). Input unit 6 is a power supply circuit that generates a direct-current voltage that ranges from approximately several volts (V) to more than ten volts (V). The present exemplary embodiment is described under the assumption that input unit 6 is not a component of voltage application device 1, but input unit 6 may be a component of voltage application device 1. Specific circuit configurations of drive circuit 21 and voltage generation circuit 22 will be described in the section "(2.3) Circuit configuration".

Figure 6:
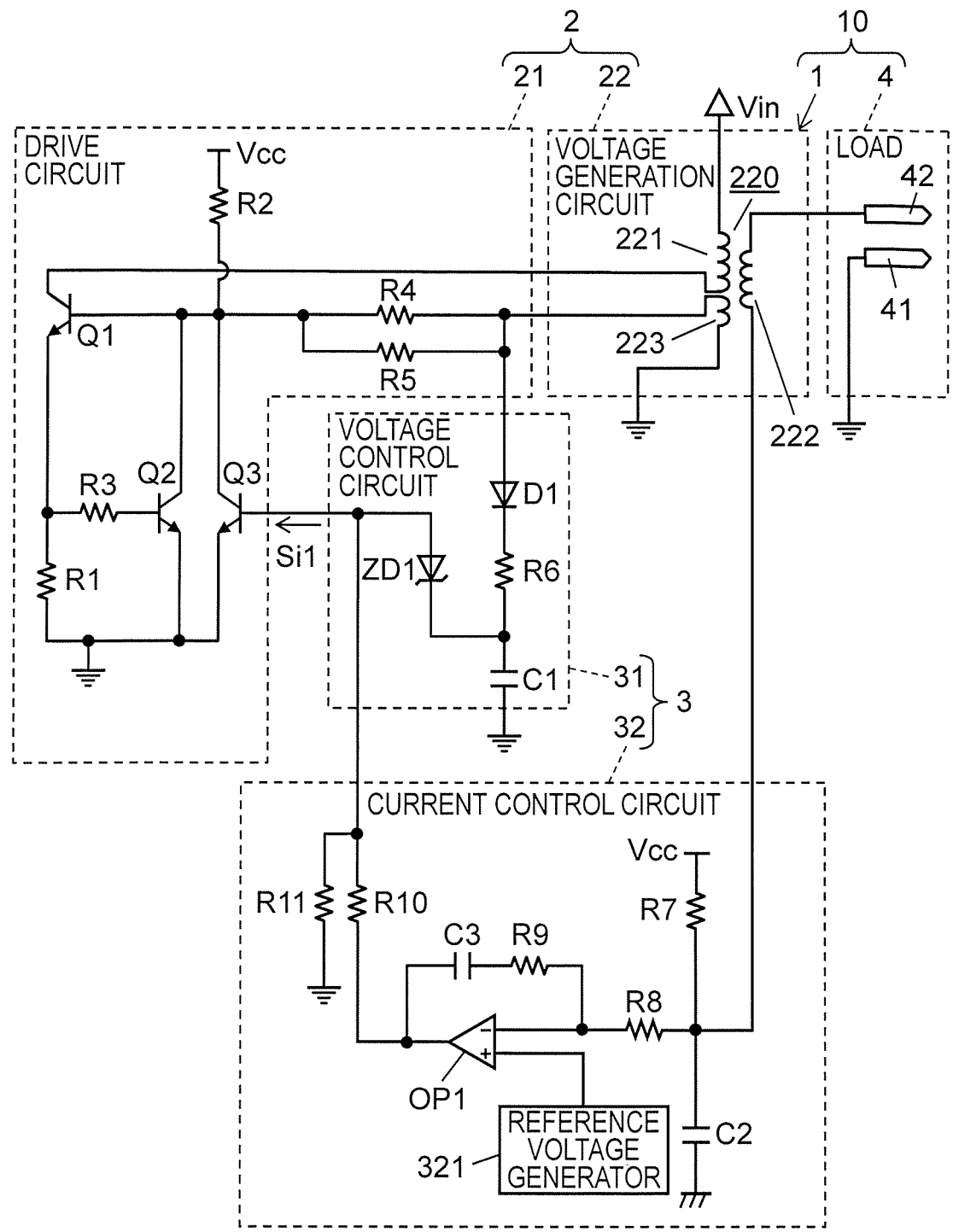
FIG. 6 is a circuit diagram illustrating an example of the discharge device according to the first exemplary embodiment.

Voltage application circuit 2 is electrically connected to load 4 (discharge electrode 41 and counter electrode 42) (see FIG. 6). Voltage application circuit 2 applies a high voltage to load 4. Here, voltage application circuit 2 is configured to apply a high voltage between discharge electrode 41 and counter electrode 42 by using discharge electrode 41 as a negative electrode (the ground) and counter electrode 42 as a positive electrode (positive). In other words, in a state where a high voltage is applied from voltage application circuit 2 to load 4, a potential difference is generated between discharge electrode 41 and counter electrode 42 in such a way that a side of counter electrode 42 has a higher potential and a side of discharge electrode 41 has a lower potential. The "high voltage" here may be a voltage that has been set in such a way that leader discharge occurs in discharge electrode 41, and is, as an example, a voltage that has a peak of approximately 6.0 kV. Note that the high voltage applied from voltage application circuit 2 to load 4 is not limited to a voltage of approximately 6.0 kV. For example, the high voltage is appropriately set according to shapes of discharge electrode 41 and counter electrode 42 or a distance between discharge electrode 41 and counter electrode 42.

Here, an operation mode of voltage application circuit 2 includes two modes, a first mode and a second mode. The first mode is a mode of increasing an applied voltage with the lapse of time, causing corona discharge to develop into dielectric breakdown, and generating a discharge current. The second mode is a mode of causing load 4 to enter into an overcurrent state and interrupting the discharge current by using control circuit 3 and the like. The "discharge current" in the present disclosure means a relatively large current that is generated after dielectric breakdown, and does not include a minute current of several μA that is generated in corona discharge before dielectric breakdown. The "overcurrent state" in the present disclosure means a state where a load decreases due to discharge and a current that is greater than or equal to an assumed value flows to load 4.

In the present exemplary embodiment, control circuit 3 controls voltage application circuit 2. Control circuit 3 controls voltage application circuit 2 in such a way that voltage application circuit 2 alternately repeats the first mode and the second mode during a drive period during which voltage application device 1 is driven. Here, control circuit 3 switches the first mode and the second mode at a drive frequency in such a way that a magnitude of an applied voltage to be applied from voltage application circuit 2 to load 4 is periodically changed at the drive frequency.

By doing this, a magnitude of electric energy that acts on liquid 50 held in discharge electrode 41 periodically changes at the drive frequency, and consequently, liquid 50 held in discharge electrode 41 mechanically vibrates at the drive frequency. Here, the drive frequency serving as a frequency of a change in the applied voltage is set to fall within a predetermined range including the resonance frequency (the natural frequency) of liquid 50 held in discharge electrode 41, as described above. The "predetermined range" in the present disclosure is a range of a frequency that causes mechanical vibration of liquid 50 to be amplified when a force (energy) applied to liquid 50 is vibrated at the frequency, and the "predetermined range" is a range obtained by specifying a lower limit value and an upper limit value by using the resonance frequency of liquid 50 as a reference. Stated another way, the drive frequency is set to have a value near the resonance frequency of liquid 50. Therefore, the mechanical vibration of liquid 50 caused by a change in the magnitude of the applied voltage has a relatively large amplitude.

In the present exemplary embodiment, control circuit 3 controls voltage application circuit 2 on the basis of a target to be monitored. The "target to be monitored" here includes at least one of an output current and an output voltage of voltage application circuit 2.

Here, control circuit 3 includes voltage control circuit 31 and current control circuit 32. Voltage control circuit 31 controls drive circuit 21 of voltage application circuit 2 on the basis of a target to be monitored including the output voltage of voltage application circuit 2. Control circuit 3 outputs control signal Si1 to drive circuit 21, and controls drive circuit 21 by using control signal Si1. Current control circuit 32 controls drive circuit 21 of voltage application circuit 2 on the basis of a target to be monitored including the output current of voltage application circuit 2. Stated another way, in the present exemplary embodiment, control circuit 3 controls voltage application circuit 2 by using both the output current and the output voltage of voltage application circuit 2 as a target to be monitored. Note that the output voltage (a secondary-side voltage) of voltage application circuit 2 and a primary-side voltage of voltage application circuit 2 have a correlation. Therefore, voltage control circuit 31 may indirectly detect the output voltage of voltage application circuit 2 on the basis of the primary-side voltage of voltage application circuit 2. Similarly, the output current (a secondary-side current) of voltage application circuit 2 and an input current (a primary-side current) of voltage application circuit 2 have a correlation. Therefore, current control circuit 32 may indirectly detect the output current of voltage application circuit 2 on the basis of the input current of voltage application circuit 2. Specific circuit configurations of voltage control circuit 31 and current control circuit 32 will be described in the section "(2.3) Circuit configuration".

Control circuit 3 is configured to cause voltage application circuit 2 to operate in the first mode when a magnitude of a target to be monitored is less than a threshold and cause voltage application circuit 2 to operate in the second mode when the magnitude of the target to be monitored is greater than or equal to the threshold. Stated another way, voltage application circuit 2 operates in the first mode until the magnitude of the target to be monitored reaches the threshold, and the applied voltage increases with the lapse of time. At this time, in discharge electrode 41, corona discharge develops into dielectric breakdown, and a discharge current is generated. When the magnitude of the target to be monitored reaches the threshold, voltage application circuit 2 operates in the second mode, and the applied voltage decreases. At this time, load 4 enters into the overcurrent state, and the discharge current is interrupted by control circuit 3 and the like. In other words, control circuit 3 and the like detect the overcurrent state of load 4 via voltage application circuit 2, and eliminate (extinguish) the discharge current by reducing the applied voltage.

By doing this, during the drive period, voltage application circuit 2 operates to alternately repeat the first mode and second mode, and the magnitude of the applied voltage periodically changes at the drive frequency. As a result, in discharge electrode 41, discharge (leader discharge) occurs that has a form of intermittently repeating a phenomenon in which corona discharge develops into dielectric breakdown. Stated another way, in discharge device 10, a discharge path is intermittently formed around discharge electrode 41 due to leader discharge, and a pulse-like discharge current is repeatedly generated.

More specifically, discharge device 10 first generates local corona discharge in liquid 50 held in distal end 411 of discharge electrode 41. In the present exemplary embodiment, discharge electrode 41 is located on a side of a negative electrode (the ground), and therefore, corona discharge generated in liquid 50 is a negative-polarity corona. Discharge device 10 causes corona discharge generated in liquid 50 to develop into higher-energy discharge. This higher-energy discharge causes dielectric breakdown (complete breakdown) to occur around discharge electrode 41, and a discharge path is formed around discharge electrode 41. In discharge device 10 according to the present exemplary embodiment, voltage application circuit 2 periodically repeats the first mode and the second mode at a drive frequency, so that dielectric breakdown intermittently occurs between discharge electrode 41 and counter electrode 42, and a discharge path that connects discharge electrode 41 and counter electrode 42 is intermittently generated.

Figure 4:
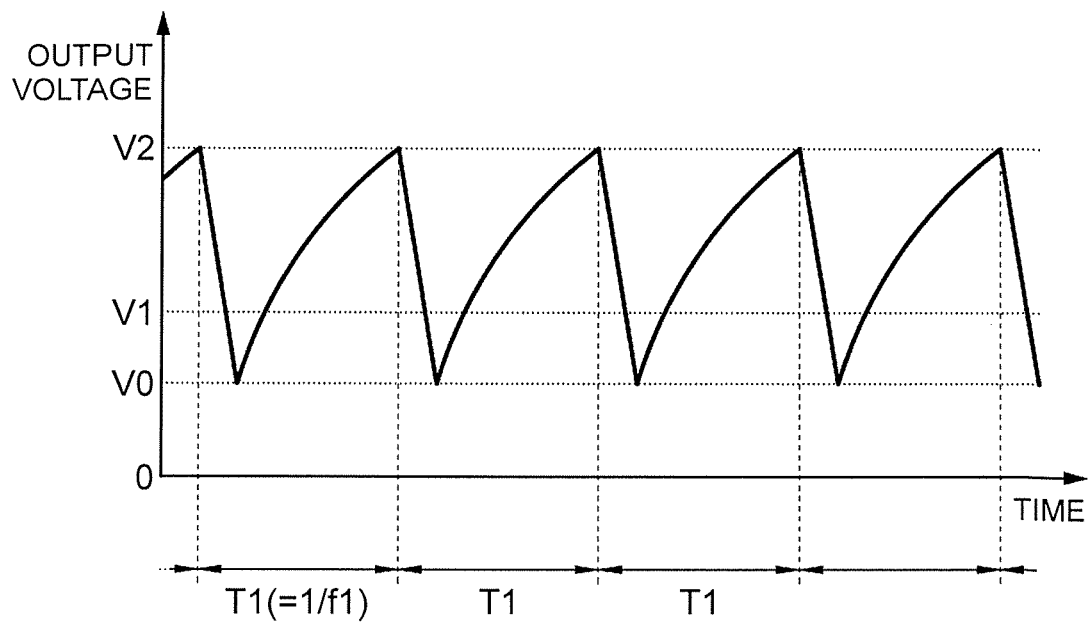
FIG. 4 is a graph schematically illustrating a discharge form of the discharge device according to the first exemplary embodiment.

In leader discharge, a discharge current that is twice to ten times larger than a discharge current of corona discharge flows through the discharge path between discharge electrode 41 and counter electrode 42. Therefore, as illustrated in FIG. 4, during a drive period, a minute current flows due to corona discharge until an applied voltage reaches maximum value V2, and when the applied voltage reaches maximum value V2, corona discharge develops into dielectric breakdown, and a relatively large discharge current instantaneously flows. In FIG. 4, a horizontal axis is a time axis, and a vertical axis indicates the output voltage (the applied voltage) of voltage application circuit 2. During a period during which the applied voltage increases before dielectric breakdown occurs, minute discharge occurs due to corona discharge. When the applied voltage reaches maximum value V2, dielectric breakdown occurs, and high-energy discharge occurs.

Here, during the drive period, if a magnitude of maximum value V2 is constant and an amount of a change in the applied voltage per unit time is constant, a cycle in which dielectric breakdown occurs in leader discharge (hereinafter also referred to as a "discharge cycle") is approximately constant. In the example of FIG. 4, dielectric breakdown periodically occurs in discharge cycle T1. Discharge cycle T1 is the same as a cycle in which the applied voltage reaches maximum value V2, and in other words, a cycle in which an operation mode of voltage application circuit 2 switches from the first mode to the second mode. In other words, as illustrated in FIG. 4, a magnitude of the applied voltage periodically changes in discharge cycle T1, and discharge cycle T1 is expressed as a reciprocal (1/f1) of drive frequency f1.

Further, in the present exemplary embodiment, a differential value between maximum value V2 and minimum value V0 of the applied voltage during the drive period is greater than or equal to ½ of maximum value V2 of the applied voltage. Stated another way, when it is assumed that a value of ½ of maximum value V2 of the applied voltage during the drive period is "V1", the differential value "V2−V0" between maximum value V2 and minimum value V0 of the applied voltage during the drive period is a value that is greater than or equal to "V1". Therefore, as illustrated in FIG. 4, minimum value V0 of the applied voltage during the drive period is less than or equal to "V1". In other words, an amplitude (V2−V0) of the applied voltage during the drive period is greater than or equal to "V1" that is ½ of maximum value V2 of the applied voltage during the drive period. In the example of FIG. 4, a differential value between maximum value V2 and minimum value V0 of the applied voltage is greater than "V1", and therefore minimum value V0 is less than "V1".

Further, in the present exemplary embodiment, the magnitude of the applied voltage changes within a range that exceeds 0 V during the drive period. Stated another way, the magnitude of the applied voltage periodically changes during the drive period, but is not less than or equal to 0 V. In other words, a waveform of the applied voltage during the drive period does not include a zero crossing point. Accordingly, in the example of FIG. 4, minimum value V0 of the applied voltage during the drive period is a value that is greater than 0 V and is less than "V1" that is ½ of maximum value V2. In addition, in the example of FIG. 4, a time period required for the applied voltage to change from minimum value V0 to maximum value V2 is sufficiently longer than a time period during which the applied voltage changes from maximum value V2 to minimum value V0. Here, when the applied voltage changes from minimum value V0 to maximum value V2, the applied voltage non-linearly changes with respect to the lapse of time in such a way that the applied voltage has a change rate that is gradually reduced (an inclination that becomes gentler) as the applied voltage gets closer to maximum value V2. In contrast, when the applied voltage changes from maximum value V2 to minimum value V0, the applied voltage roughly linearly changes with respect to the lapse of time.

Meanwhile, drive frequency f1 is set to fall within a predetermined range including resonance frequency fr (a natural frequency) of liquid 50 held in discharge electrode 41, as described above. Resonance frequency fr1 of liquid 50 depends, for example, on a volume (an amount) of liquid 50, and is expressed according to formula 1 described below by using volume Vol of liquid 50 held in discharge electrode 41 and coefficient α. Coefficient α depends on a surface tension, a viscosity, and the like of liquid 50 held in discharge electrode 41.

$$fr1 = \alpha \times \sqrt{Vol}$$ [Formula 1]

Figure 5:
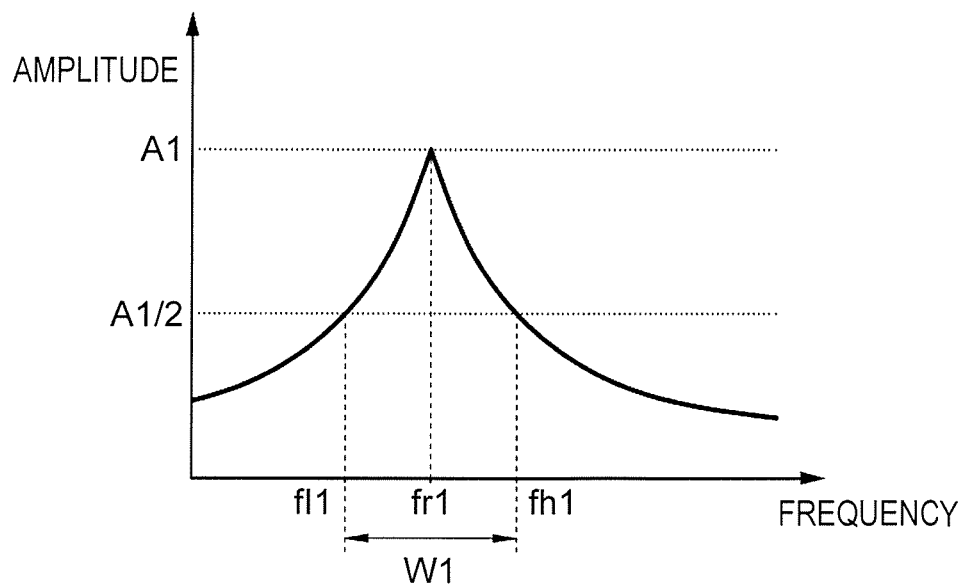
FIG. 5 is a graph schematically illustrating a frequency characteristic of liquid in the discharge device according to the first exemplary embodiment.

Stated another way, in a case where liquid 50 has, for example, a frequency characteristic illustrated in FIG. 5, drive frequency f1 is set to fall within predetermined range W1 with resonance frequency fr1 of liquid 50 as a reference. FIG. 5 schematically illustrates a frequency characteristic of mechanical vibration of liquid 50 under the assumption that a horizontal axis indicates a frequency (a vibration frequency), a vertical axis indicates an amplitude, and an amplitude at resonance frequency fr1 is "A1". Here, it is preferable that predetermined range W1 be a range of full width at half maximum (FWHM) in a frequency characteristic of vibration of liquid 50. In short, in the example of FIG. 5, when it is assumed that frequency fl1, is a frequency at which an amplitude on a lower-frequency side of resonance frequency fr1 is "A1/2" (½ of "A1") and frequency fh1 is a frequency at which an amplitude on a higher-frequency side of resonance frequency fr1 is "A1/2", a range between frequency fl1 and frequency fh1 is predetermined range W1. In other words, a lower limit value of predetermined range W1 is expressed as "fl1", and an upper limit value is expressed as "fh1". By setting drive frequency f1 to fall within predetermined range W1 specified as described above, drive frequency f1 is set to have a value near resonance frequency fr1 of liquid 50.

In the present exemplary embodiment, it is assumed, as an example, that liquid 50 held in discharge electrode 41 is "water" (dew condensation water) and is a droplet that has adhered to a surface of distal end 411 of discharge electrode 41, has a semispherical shape, and has a volume of "50 nL". It is assumed that resonance frequency fr1 of liquid 50 in this case is 1 kHz. In this case, it is preferable that drive frequency f1 be set to fall within predetermined range W1 within which a lower limit value is 600 Hz, 60% of resonance frequency fr1 of liquid 50, and an upper limit value is 1.4 kHz, 140% of resonance frequency fr1 of liquid 50. In this case, it is more preferable that the lower limit value of predetermined range W1 be 750 Hz, 75% of resonance frequency fr1 of liquid 50. It is also more preferable that the upper limit value of predetermined range W1 be 1.25 kHz, 125% of resonance frequency fr1 of liquid 50. In addition, in this case, it is more preferable that the lower limit value of predetermined range W1 be 800 Hz, 80% of resonance frequency fr1 of liquid 50. It is also more preferable that the upper limit value of predetermined range W1 be 1.2 kHz, 120% of resonance frequency fr1 of liquid 50. In the present exemplary embodiment, it is assumed, as an example, that drive frequency f1 has been set to have the same value (1 kHz) as a value of resonance frequency fr1.

In addition, discharge device 10 according to the present exemplary embodiment applies a voltage to load 4 from voltage application circuit 2 in a state where liquid 50 serving as dew condensation water is supplied to (held in) discharge electrode 41. By doing this, in load 4, leader discharge occurs between discharge electrode 41 and counter electrode 42 due to a potential difference between discharge electrode 41 and counter electrode 42. At this time, liquid 50 held in discharge electrode 41 is electrostatically atomized due to discharge. As a result, in discharge device 10, nanometer-sized charged fine particle liquid containing radicals is generated. The generated charged fine particle liquid is ejected around discharge device 10, for example, through opening 421 of counter electrode 42.

(2.2) Leader Discharge

Next, leader discharge is described in more detail.

In general, when energy is input between a pair of electrodes and discharge is generated, a discharge form changes from corona discharge to glow discharge or arc discharge according to an amount of input energy.

Corona discharge is discharge that locally occurs in one electrode, and is discharge without dielectric breakdown between the pair of electrodes. Glow discharge and arc discharge are discharge with dielectric breakdown between the pair of electrodes. In glow discharge and arc discharge, while energy is input between the pair of electrodes, a discharge path formed due to dielectric breakdown is maintained, and a discharge current is continuously generated between the pair of electrodes. If a capacity per unit time of a current that can be supplied between the pair of electrodes from a power supply (voltage application circuit 2) is sufficiently large, a discharge path that has been formed once is maintained without interruption, and corona discharge develops into glow discharge or arc discharge, as described above.

Leader discharge is also discharge with dielectric breakdown between the pair of electrodes. However, in leader discharge, dielectric breakdown does not continuously occur, but intermittently occurs. Therefore, a discharge current generated between the pair of electrodes is also intermittently generated. Stated another way, for example, in a case where the power supply (voltage application circuit 2) does not have a current capacity required to maintain the discharge path, as described above, as soon as corona discharge develops into dielectric breakdown, a voltage applied between the pair of electrodes decreases, the discharge path is interrupted, and discharge stops. Due to the repetition of the occurrence and stop of discharge, as described above, the discharge current intermittently flows. As described above, leader discharge repeats a high discharge energy state and a low discharge energy state. In this respect, leader discharge is different from glow discharge and arc discharge in which dielectric breakdown continuously occurs (stated another way, the discharge current is continuously generated).

In leader discharge, a large number of radicals are generated that corresponds to approximately two to ten times the number of radicals generated in corona discharge. However, a generation amount of ozone is reduced to be nearly equal to a generation amount of ozone in the case of corona discharge. A conceivable reason for this is that part of ozone is broken due to exposition to high-energy leader discharge when ozone generated due to leader discharge is emitted.

(2.3) Circuit Configuration

Next, a specific circuit configuration of voltage application device 1 is described with reference to FIG. 6. FIG. 6 is a circuit diagram schematically illustrating an example of a circuit configuration of discharge device 10. In FIG. 6, illustration of input unit 6 is omitted.

Voltage application circuit 2 includes drive circuit 21 and voltage generation circuit 22, as described above. In the example of FIG. 6, voltage application circuit 2 is an insulated direct current to direct current (DC/DC) converter. Voltage application circuit 2 boosts input voltage Vin (for example, 13.8 V) from input unit 6 (see FIG. 1), and outputs the boosted voltage as an output voltage. The output voltage of voltage application circuit 2 is applied as an applied voltage to load 4 including discharge electrode 41 and counter electrode 42.

Voltage generation circuit 22 includes isolation transformer 220 that includes primary coil 221, secondary coil 222, and auxiliary coil 223. Primary coil 221 and auxiliary coil 223 are electrically insulated against secondary coil 222, and primary coil 221 and auxiliary coil 223 are magnetically coupled. One end of secondary coil 222 is electrically connected to counter electrode 42.

Drive circuit 21 includes transistor Q1, and supplies power to primary coil 221 of isolation transformer 220 due to a switching operation of transistor Q1. Drive circuit 21 includes transistor Q2, transistor Q3, and resistors R1 to R5 in addition to transistor Q1. Transistors Q1, Q2, Q3 are configured, as an example, by an npn bipolar transistor.

A collector of transistor Q1 is connected to primary coil 221, and an emitter of transistor Q1 is connected to the ground via resistor R1. Input voltage Vin is applied to a series circuit of primary coil 221, transistor Q1, and resistor R1 from input unit 6. A base of transistor Q1 is connected to control power supply Vcc via resistor R2. Control power supply Vcc applies a control voltage (for example, 5.1 V) to drive circuit 21.

Collectors of transistors Q2, Q3 are connected to the base of transistor Q1. Emitters of transistors Q2, Q3 are connected to the ground. A base of transistor Q2 is connected to the emitter of transistor Q1 via resistor R3. The base of transistor Q1 is connected to one end of auxiliary coil 223 via a parallel circuit of resistors R4, R5. Another end of auxiliary coil 223 is connected to the ground. A base of transistor Q3 is connected to control circuit 3 including voltage control circuit 31 and current control circuit 32, and control signal Si1. is input to the base of transistor Q3 from control circuit 3.

According to the configuration described above, voltage application circuit 2 configures a self-excited converter. Stated another way, when transistor Q1 is turned on and a current flows to primary coil 221 of isolation transformer 220, a voltage across resistor R1 increases, and transistor Q2 is turned on. By doing this, the base of transistor Q1 is connected to the ground via transistor Q2, and therefore transistor Q1 is turned off. When transistor Q1 is turned off, the current that flows through primary coil 221 is interrupted, the voltage across resistor R1 decreases, and transistor Q2 is turned off. By doing this, a high voltage is induced to secondary coil 222 of isolation transformer 220, and the high voltage is applied to load 4 as an output voltage of voltage application circuit 2. At this time, voltage is also induced to auxiliary coil 223 due to an induced voltage generated in secondary coil 222, a voltage between the base and the emitter of transistor Q1 increases, and transistor Q1 is turned on. Voltage application circuit 2 repeats the operation described above to boost input voltage Vin, and applies an output voltage to load 4.

Control circuit 3 includes voltage control circuit 31 and current control circuit 32, as described above.

Voltage control circuit 31 includes diode D1, resistor R6, capacitor C1, and Zener diode ZD1. An anode of diode D1 is connected to a connecting point of auxiliary coil 223 and resistors R4, R5. A cathode of diode D1 is connected to one end of capacitor C1 via resistor R6. Another end of capacitor C1 is connected to the ground. Further, the one end of capacitor C1 (a connecting point of capacitor C1 and resistor R6) is connected to a cathode of Zener diode ZD1. An anode of Zener diode ZD1 is connected to the base of transistor Q3 of drive circuit 21 as an output terminal of voltage control circuit 31.

In the configuration described above, voltage control circuit 31 monitors an induced voltage of auxiliary coil 223 to indirectly monitor the output voltage of voltage application circuit 2 (the induced voltage of secondary coil 222) serving as a target to be monitored. Stated another way, while the output voltage of voltage application circuit 2 is less than maximum value V2, Zener diode ZD1 of voltage control circuit 31 is in an OFF state. If the output voltage of voltage application circuit 2 becomes greater than or equal to maximum value V2, Zener diode ZD1 of voltage control circuit 31 is turned on. At this time, control signal Si1 exceeds a control threshold, voltage is applied between the base and the emitter of transistor Q3 of drive circuit 21, and transistor Q3 is turned on. By doing this, a base current of transistor Q1 flows to the ground via transistor Q3, and therefore a collector current of transistor Q1 decreases. Therefore, if the output voltage of voltage application circuit 2 is greater than or equal to maximum value V2, voltage control circuit 31 reduces energy to be input from drive circuit 21 of voltage application circuit 2 to voltage generation circuit 22.

Current control circuit 32 includes operational amplifier OP1, reference voltage generator 321, resistors R7 to R11, and capacitors C2, C3. One end of capacitor C2 is connected to control power supply Vcc via resistor R7. Another end of capacitor C2 is connected to the ground. Control power supply Vcc applies a control voltage (for example, 5.1 V) to a series circuit of resistor R7 and capacitor C2. A connecting point of resistor R7 and capacitor C2 (the one end of capacitor C2) is connected to an inverted input terminal of operational amplifier OP1 via resistor R8. In addition, the connecting point of resistor R7 and capacitor C2 is connected to an end (another end) on an opposite side of counter electrode 42 in secondary coil 222 of isolation transformer 220. In other words, control power supply Vcc is connected to counter electrode 42 via resistor R7 and secondary coil 222. A non-inverted input terminal of operational amplifier OP1 is connected to reference voltage generator 321, and a reference voltage is input to the non-inverted input terminal from reference voltage generator 321. A series circuit of resistor R9 and capacitor C3 is connected between the inverted input terminal and an output terminal of operational amplifier OP1. The output terminal of operational amplifier OP1 is connected to one end of resistor R10. Another end of resistor R10 is connected to the ground via resistor R11. A connecting point of resistor R10 and resistor R11 (the other end of resistor R10) is connected to the base of transistor Q3 of drive circuit 21 as an output terminal of current control circuit 32.

In the configuration described above, current control circuit 32 monitors an induced current of secondary coil 222 of voltage generation circuit 22 to monitor an output current of voltage application circuit 2 (the induced voltage of secondary coil 222) serving as a target to be monitored. Stated another way, while the output current of voltage application circuit 2 is less than a threshold, an output of operational amplifier OP1 of current control circuit 32 has a low level (L-level). If the output current of voltage application circuit 2 becomes greater than or equal to the threshold, the output of operational amplifier OP1 of current control circuit 32 has a high level (H-level). At this time, control signal Si1 exceeds the control threshold, voltage is applied between the base and the emitter of transistor Q3 of drive circuit 21, and transistor Q3 is turned on. By doing this, the base current of transistor Q1 flows to the ground via transistor Q3, and therefore the collector current of transistor Q1 decreases. Therefore, if the output current of voltage application circuit 2 is greater than or equal to the threshold, current control circuit 32 reduces energy to be input from drive circuit 21 of voltage application circuit 2 to voltage generation circuit 22.

(2.4) Operation

In the circuit configuration illustrated in FIG. 6, control circuit 3 performs an operation described below, so that discharge device 10 generates leader discharge between discharge electrode 41 and counter electrode 42. Stated another way, during a period before dielectric breakdown occurs, control circuit 3 uses the output voltage of voltage application circuit 2 as a target to be monitored. When the output voltage serving as a target to be monitored becomes greater than or equal to maximum value V2, control circuit 3 causes voltage control circuit 31 to reduce energy to be input to voltage generation circuit 22. In contrast, after the occurrence of dielectric breakdown, control circuit 3 uses the output current of voltage application circuit 2 as a target to be monitored. When the output current serving as a target to be monitored becomes greater than or equal to the threshold, control circuit 3 causes current control circuit 32 to reduce energy to be input to voltage generation circuit 22. By doing this, an applied voltage is reduced, and voltage application circuit 2 operates in the second mode of causing load 4 to enter into an overcurrent state and interrupting a discharge current. Stated another way, an operation mode of voltage application circuit 2 switches from the first mode to the second mode.

At this time, both the output voltage and the output current of voltage application circuit 2 decrease, and therefore control circuit 3 restarts a switching operation of drive circuit 21. By doing this, voltage application circuit 2 operates in the first mode of increasing the applied voltage with the lapse of time, causing corona discharge to develop into dielectric breakdown, and generating a discharge current. Stated another way, the operation mode of voltage application circuit 2 switches from the second mode to the first mode.

After current control circuit 32 has operated, and in other words, after an output of operational amplifier OP1 has become the H-level, a rate of an increase in the output voltage (the applied voltage) of voltage application circuit 2 is determined according to an influence of an integration circuit including operational amplifier OP1, resistor R9, and capacitor C3. In short, in the example of FIG. 4, an amount of a change in the applied voltage per unit time in discharge cycle T1 is determined on the basis of a time constant of the integration circuit including operational amplifier OP1, resistor R9, and capacitor C3. Maximum value V2 is a fixed value. Therefore, in other words, discharge cycle T1 is determined on the basis of the time constant of the integration circuit including operational amplifier OP1, resistor R9, and capacitor C3.

In the present exemplary embodiment, drive frequency f1 is set to fall within predetermined range W1 with resonance frequency fr1 of liquid 50 as a reference. As described above, discharge cycle T1 is expressed as a reciprocal (1/f1) of drive frequency f1. Therefore, the time constant of the integration circuit including operational amplifier OP1, resistor R9, and capacitor C3, or the like is determined in such a way that drive frequency f1 that is a reciprocal (1/T1) of discharge cycle T1 is set to fall within predetermined range W1 with resonance frequency fr1 of liquid 50 as a reference.

During the drive period, control circuit 3 repeats the operation described above, so that voltage application circuit 2 operates to alternately repeat the first mode and the second mode. Therefore, during the drive period, a magnitude of an applied voltage applied to load 4 including discharge electrode 41 from voltage application circuit 2 periodically changes at drive frequency f1 within predetermined range W1 including resonance frequency fr1 of liquid 50. In the present exemplary embodiment, as an example, drive frequency f1 has been set to have the same value (1 kHz) as a value of resonance frequency fr1. By doing this, a magnitude of electric energy that acts on liquid 50 held in discharge electrode 41 periodically changes at drive frequency f1, and liquid 50 mechanically vibrates at drive frequency f1.

In short, the applied voltage is applied to load 4 including discharge electrode 41 from voltage application circuit 2, so that a force caused by an electric field acts on liquid 50 held in discharge electrode 41, and liquid 50 is transformed. At this time, force F1 that acts on liquid 50 held in discharge electrode 41 is expressed as a product of charge amount q1 included in liquid 50 and electric field E1 (F1=q1×E1). In particular, in the present exemplary embodiment, the applied voltage is applied between counter electrode 42 that faces distal end 411 of discharge electrode 41 (see FIG. 3B) and discharge electrode 41, and therefore, a force acts on liquid 50 in a direction in which liquid 50 is pulled toward counter electrode 42 due to the electric field. As a result, as illustrated in FIG. 2A, liquid 50 held in distal end 411 of discharge electrode 41 receives the force caused by the electric field to expand toward counter electrode 42 along an axis where discharge electrode 41 and counter electrode 42 face each other, and liquid 50 has a conical shape called a Taylor cone. When the applied voltage applied to load 4 decreases from the state illustrated in FIG. 2A, a force that acts on liquid 50 due to an influence of the electric field also decreases, and liquid 50 is transformed. As a result, as illustrated in FIG. 2B, liquid 50 held in distal end 411 of discharge electrode 41 contracts along the axis where discharge electrode 41 and counter electrode 42 face each other.

Figure 2B:
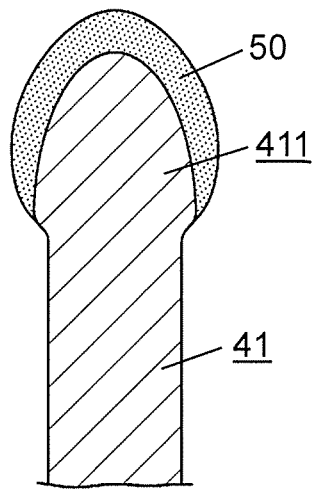
FIG. 2B is a schematic diagram illustrating a state where the liquid held in the discharge electrode has contracted in the discharge device.

Due to a periodical change at drive frequency f1 in the magnitude of the applied voltage, liquid 50 held in discharge electrode 41 is alternately transformed between the shape illustrated in FIG. 2A and the shape illustrated in FIG. 2B. The electric field is concentrated on a distal end (a vertex) of the Taylor cone, so that discharge occurs. Therefore, dielectric breakdown occurs in a state where the distal end of the Taylor cone is pointed, as illustrated in FIG. 2A. Accordingly, discharge intermittently occurs in accordance with drive frequency f1. As a result, in discharge electrode 41, leader discharge occurs in which a phenomenon in which corona discharge develops into dielectric breakdown is intermittently repeated.

Meanwhile, when drive frequency f1 becomes higher in order to match resonance frequency fr1 of liquid 50, and in other words, when discharge cycle T1 becomes shorter, there is a possibility of an increase in a generation amount of ozone that is generated when radicals are generated due to leader discharge. Stated another way, when drive frequency f1 becomes higher, in some cases, a time interval of the occurrence of dielectric breakdown becomes shorter, the number of times of the occurrence of discharge per unit time (for example, one second) increases, and the number of generated radicals and a generation amount of ozone per unit time increase. The following two means are examples of a means for suppressing an increase in a generation amount of ozone per unit time resulting from an increase in drive frequency f1.

A first means is reducing maximum value V2 of the applied voltage. Stated another way, maximum value V2 of the applied voltage during a drive period is adjusted to be less than or equal to a specified voltage value in such a way that a generation amount of ozone per unit time resulting from discharge generated in discharge electrode 41 during the drive period is less than or equal to a specified value. By reducing maximum value V2 of the applied voltage to be less than or equal to the specified voltage value, a generation amount of ozone generated when radicals are generated due to leader discharge is reduced. By doing this, an increase in a generation amount of ozone due to an increase in drive frequency f1 can be suppressed.

A second means is increasing a volume of liquid 50 held in discharge electrode 41. Stated another way, the volume of liquid 50 during a drive period is adjusted to be greater than or equal to a specified volume in such a way that a generation amount of ozone per unit time resulting from discharge generated in discharge electrode 41 during the drive period is less than or equal to a specified value. Due to an increase in the volume of liquid 50 held in discharge electrode 41, a generation amount of ozone generated when radicals are generated due to leader discharge is reduced. By doing this, an increase in a generation amount of ozone due to an increase in drive frequency f1 can be suppressed.

In discharge device 10 according to the present exemplary embodiment, an increase in a generation amount of ozone per unit time is suppressed according to the first means, and in other words, by reducing maximum value V2 of the applied voltage during the drive period. By doing this, in discharge device 10, for example, a concentration of ozone can be reduced to approximately 0.02 ppm. Note that discharge device 10 may employ the second means, or may employ both the first means and the second means.

(3) Variations

The first exemplary embodiment is merely one of various exemplary embodiments of the present disclosure. Various changes can be made to the first exemplary embodiment according to design or the like, if an object of the present disclosure can be achieved. Variations of the first exemplary embodiment are enumerated below. Variations described below can be applied in appropriate combination with each other.

(3.1) First Variation

In voltage application device 1 in a first variation, voltage application circuit 2 is configured in such a way that drive frequency f1 can be changed within predetermined range W1. Stated another way, drive frequency f1 that specifies a change cycle of an applied voltage does not always have a fixed value, and may have a variable value. For example, drive frequency f1 may be manually changed by a user, or may be automatically changed by control circuit 3.

In a case where drive frequency f1 is changed by a user, voltage application device 1 further includes an operation unit that receives an operation performed by the user. Control circuit 3 adjusts drive frequency f1 according to the operation performed on the operation unit by the user. An operation may be performed on the operation unit during an operation of voltage application device 1 (a drive period), or may be performed, for example, in manufacturing voltage application device 1. In a case where an operation is performed on the operation unit in manufacturing voltage application device 1, a user who performs the operation on the operation unit is a manufacturer of voltage application device 1.

In a case where control circuit 3 automatically changes drive frequency f1, control circuit 3 changes drive frequency f1, for example, on the basis of at least one of the output current and the output voltage of voltage application circuit 2 that is a target to be monitored. For example, in a case where discharge (leader discharge) does not stably occur, control circuit 3 determines an abnormality on the basis of a target to be monitored, and control circuit 3 changes drive frequency f1 in such a way that drive frequency f1 becomes closer to resonance frequency fr1 of liquid 50.

Here, a change in drive frequency f1 is achieved, for example, by changing a circuit constant (a resistance value or a capacitance value) of resistor R9, capacitor C3, or the like in control circuit 3 illustrated in FIG. 6. Stated another way, drive frequency f1 is determined according to a time constant of an integration circuit including operational amplifier OP1, resistor R9, and capacitor C3, and therefore drive frequency f1 is changed by changing a circuit constant of operational amplifier OP, resistor R9, or capacitor C3. A configuration in which the circuit constant is changed is not restrictive, and drive frequency f1 may be changed by using, for example, a microcomputer. Stated another way, in a case where control circuit 3 includes a microcomputer, a change in drive frequency f1 is achieved, for example, by changing a duty ratio of a pulse width modulation (PWM) signal that is output from the microcomputer.

(3.2) Other Variations

Liquid supply unit 5 that generates charged fine particle liquid is omitted from discharge device 10. In this case, discharge device 10 generates air ion serving as an active ingredient due to leader discharge generated between discharge electrode 41 and counter electrode 42.

Counter electrode 42 may be omitted from discharge device 10. In this case, leader discharge occurs between discharge electrode 41 and a member, such as a housing, that is present around discharge electrode 41. Further, both liquid supply unit 5 and counter electrode 42 may be omitted from discharge device 10.

In addition, liquid supply unit 5 is not always configured to cool down discharge electrode 41 and generate dew condensation water in discharge electrode 41, as in the first exemplary embodiment. Liquid supply unit 5 may be configured to supply liquid 50 to discharge electrode 41 from a tank by using, for example, a capillarity phenomenon or a supply mechanism such as a pump. Further, liquid 50 is not limited to water (including dew condensation water), and may be liquid other than water.

In addition, voltage application circuit 2 may be configured to apply a high voltage between discharge electrode 41 and counter electrode 42 by using discharge electrode 41 as a positive electrode (positive) and counter electrode 42 as a negative electrode (the ground). Further, it is sufficient if a potential difference (voltage) is generated between discharge electrode 41 and counter electrode 42. Therefore, voltage application circuit 2 may apply a negative voltage to load 4 by grounding an electrode on a higher-potential side (a positive electrode) and causing an electrode on a lower-potential side (a negative electrode) to have a negative potential. Stated another way, voltage application circuit 2 may ground discharge electrode 41, and may cause counter electrode 42 to have a negative potential. Alternatively, voltage application circuit 2 may cause discharge electrode 41 to have a negative potential, and may ground counter electrode 42.

In addition, voltage application device 1 may include a limiting resistor between voltage application circuit 2 and discharge electrode 41 or counter electrode 42 in load 4. The limiting resistor is a resistor that limits a peak value of a discharge current that flows after dielectric breakdown in leader discharge. The limiting resistor is electrically connected, for example, between voltage application circuit 2 and discharge electrode 41 or between voltage application circuit 2 and counter electrode 42.

FIG. 6 merely illustrates an example of a circuit configuration of discharge device 10, and a specific circuit configuration of voltage application device 1 can be appropriately changed. For example, voltage application circuit 2 is not limited to a self-excited converter, and may be a separately excited converter. In addition, in voltage application circuit 2, transistors Q1, Q2, Q3 are not limited to bipolar transistors, and may be, for example, metal-oxide-semiconductor field effect transistors (MOSFETs) or the like. Furthermore, voltage generation circuit 22 may be implemented by a transformer (a piezoelectric transformer) including a piezoelectric element.

FIG. 4 merely illustrates an example of a waveform of an applied voltage during a drive period, and the waveform of the applied voltage may be, for example, a sawtooth waveform. In this case, when the applied voltage changes from minimum value V0 to maximum value V2, the applied voltage roughly linearly changes with respect to the lapse of time.

In addition, it is not an essential configuration in voltage application device 1 that minimum value V0 of the applied voltage during the drive period is greater than 0 V and is less than "V1" that is ½ of maximum value V2 of the applied voltage. For example, minimum value V0 of the applied voltage during the drive period may be greater than or equal to "V1" that is ½ of maximum value V2 of the applied voltage, or may be less than 0 V.

Further, functions that are similar to functions of voltage application device 1 according to the first exemplary embodiment may be implemented by a method for controlling voltage application circuit 2, a computer program, a recording medium that has recorded the computer program, or the like. Stated another way, functions that correspond to control circuit 3 may be implemented by a method for controlling voltage application circuit 2, a computer program, a recording medium that has recorded the computer program, or the like.

Furthermore, in a comparison between two values, such as a target to be monitored and a threshold, the phrase "greater than or equal to" includes both a case where the two values are equal to each other and a case where one of the two values exceeds another. However, this is not restrictive, and the phrase "greater than or equal to" here may be a synonym to the phrase "greater than" that only includes a case where one of the two values exceeds another. Stated another way, whether a case where the two values are equal to each other is included can be arbitrarily changed depending on setting of a threshold or the like. Therefore, there is no technical difference between the phrase "greater than or equal to" and the phrase "greater than". Similarly, the phrase "less than" may be a synonym to the phrase "less than or equal to".

Second Exemplary Embodiment

Figure 7:
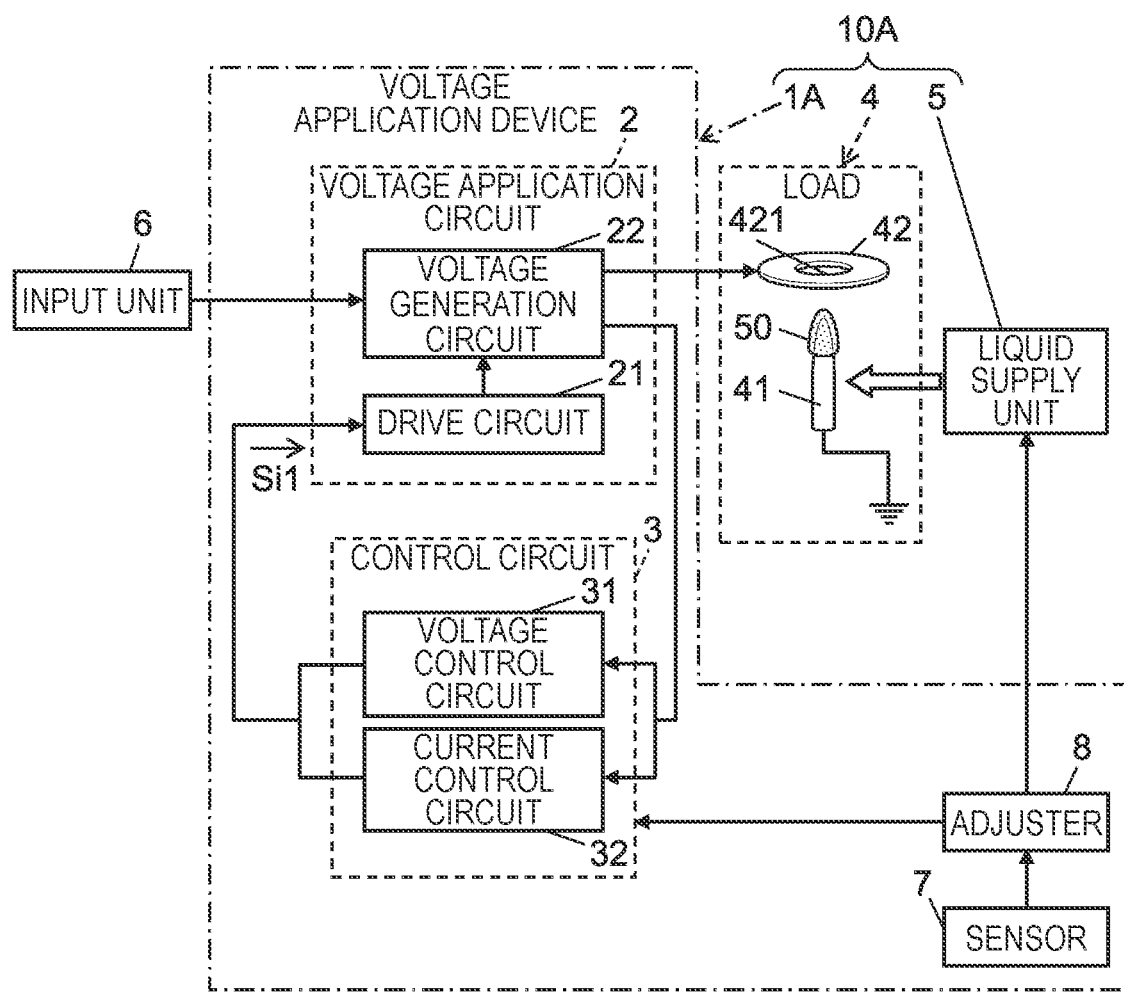
FIG. 7 is a block diagram of a discharge device according to a second exemplary embodiment.

Discharge device 10A according to the present exemplary embodiment is different from discharge device 10 according to the first exemplary embodiment in that sensor 7 is further included that measures at least one of a temperature and a humidity, as illustrated in FIG. 7. Hereinafter, description of a configuration that is similar to a configuration according to the first exemplary embodiment is appropriately omitted by using common reference numerals.

Sensor 7 is a sensor that detects a state around discharge electrode 41. Sensor 7 detects information relating to an environment (a state) around discharge electrode 41. The environment (the state) around discharge electrode 41 includes at least one of a temperature and a humidity (relative humidity). The environment (the state) around discharge electrode 41 that is a target to be detected by sensor 7 includes, for example, an odor index, illuminance, the presence or absence of a person, and the like in addition to temperature and humidity. The present exemplary embodiment is described under the assumption that voltage application device 1A includes sensor 7 as a component, but sensor 7 may be omitted from components of voltage application device 1A.

Discharge device 10A according to the present exemplary embodiment further includes adjuster 8. Adjuster 8 adjusts at least one of drive frequency f1 and a generation amount of liquid 50 (dew condensation water) in liquid supply unit 5 on the basis of an output of sensor 7. The present exemplary embodiment is described under the assumption that voltage application device 1A includes adjuster 8 as a component, but adjuster 8 may be omitted from components of voltage application device 1A.

As described in the first exemplary embodiment, resonance frequency fr1 (a natural frequency) of liquid 50 depends, for example, on a volume (an amount) of liquid 50. In contrast, liquid supply unit 5 cools down discharge electrode 41 by using cooler 51 (see FIG. 3B) to generate liquid 50 (dew condensation water) in discharge electrode 41. Therefore, when a temperature or humidity around discharge electrode 41 changes, a generation amount of liquid 50 also changes. Accordingly, by adjusting at least one of drive frequency f1 and a generation amount of liquid 50 in liquid supply unit 5 on the basis of at least one of a temperature and a humidity, drive frequency f1 can be caused to be closer to resonance frequency fr1 of liquid 50 regardless of temperature and humidity.

In the present exemplary embodiment, adjuster 8 has functions of both a frequency adjuster that adjusts drive frequency f1 on the basis of an output of sensor 7 and a generation amount adjuster that adjusts a generation amount of liquid 50 (dew condensation water) in liquid supply unit 5 on the basis of the output of sensor 7. Specifically, voltage application device 1A includes a microcomputer, and adjuster 8 is implemented by this microcomputer. Stated another way, the microcomputer serving as adjuster 8 obtains the output of sensor 7 (hereinafter also referred to as a "sensor output"), and adjusts at least one of drive frequency f1 and a generation amount of liquid 50 in liquid supply unit 5 in accordance with the sensor output.

In a case where this adjuster 8 functions as the frequency adjuster, adjuster 8 adjusts drive frequency f1 on the basis of the output of sensor 7. Adjuster 8 increases drive frequency f1, for example, as a temperature or humidity around discharge electrode 41 increases. By doing this, for example, in a situation where humidity is high and a generation amount of liquid 50 (dew condensation water) increases, drive frequency f1 can be caused to be closer to resonance frequency fr1 of liquid 50 by increasing drive frequency f1 in accordance with an increase in a volume of liquid 50 held in discharge electrode 41. Adjustment of drive frequency f1 is achieved, for example, by changing a circuit constant (a resistance value or a capacitance value) of resistor R9, capacitor C3, or the like in control circuit 3.

In a case where adjuster 8 functions as the generation amount adjuster, adjuster 8 adjusts a generation amount of liquid 50 (dew condensation water) in liquid supply unit 5 on the basis of the output of sensor 7. Adjuster 8 decreases the generation amount of liquid 50 in liquid supply unit 5, for example, as a temperature or humidity around discharge electrode 41 increases. By doing this, for example, in a situation where humidity is high and the generation amount of liquid 50 increases, drive frequency f1 can be caused to be closer to resonance frequency fr1 of liquid 50 by reducing the generation amount of liquid 50 in liquid supply unit 5. Adjustment of the generation amount of liquid 50 in liquid supply unit 5 is achieved, for example, by changing a set temperature of cooler 51 by using a value of a current applied to a pair of Peltier elements 511.

In addition, it is not an essential configuration in discharge device 10A that adjuster 8 has functions of both the frequency adjuster and the generation amount adjuster, as described in the second exemplary embodiment. Stated another way, adjuster 8 may only have a function of either the frequency adjuster or the generation amount adjuster.

A configuration (including variations) described in the second exemplary embodiment can be applied in appropriate combination of a configuration (including variations) described in the first exemplary embodiment.

(Conclusion)

As described above, voltage application device 1, 1A in a first aspect includes voltage application circuit 2. Voltage application circuit 2 applies a voltage to load 4 including discharge electrode 41 that holds liquid 50, and voltage application circuit 2 generates discharge in the discharge electrode 41. During a drive period, voltage application circuit 2 periodically changes a magnitude of the voltage applied to load 4 at drive frequency f1 within predetermined range W1 including resonance frequency fr1 of liquid 50, and voltage application circuit 2 mechanically vibrates liquid 50.

According to this configuration, liquid 50 mechanically vibrates at drive frequency f1 near resonance frequency fr1 of liquid 50 to vibrate at a relatively large amplitude. Therefore, when an electric field acts on liquid 50, a distal end has a more sharply pointed shape. Accordingly, in liquid 50, a field intensity required for dielectric breakdown is reduced, and discharge more easily occurs, in comparison with a case where liquid 50 mechanically vibrates at a frequency away from resonance frequency fr1 of liquid 50. Therefore, for example, even when there is a variation in a magnitude of a voltage applied from voltage application circuit 2 to load 4, a variation in a shape of discharge electrode 41, a variation in an amount of liquid 50 supplied to discharge electrode 41, or another variation, discharge can stably occur. As a result, there is an advantage by which voltage application device 1, 1A can more stably generate discharge.

In voltage application device 1, 1A in a second aspect, in the first aspect, a differential value between maximum value V2 and minimum value V0 of an applied voltage during the drive period is greater than or equal to ½ of maximum value V2 of the voltage.

According to this configuration, an amplitude of the voltage applied to load 4 can be relatively increased to a value that is maximum value V2 —minimum value V0. Therefore, an amplitude of mechanical vibration of liquid 50 due to a change in a magnitude of a voltage applied voltage can be further increased.

In voltage application device 1, 1A in a third aspect, in the first or second aspect, the magnitude of the applied voltage changes within a range that exceeds 0 V during the drive period.

According to this configuration, during the drive period, an electric field can be caused to continuously act on liquid 50 held in discharge electrode 41 without interruption. Therefore, a behavior that deviates from resonance of liquid 50 can be reduced.

In voltage application device 1, 1A in a fourth aspect, in any of the first to third aspects, predetermined range W1 is a range of full width at half maximum (FWHM) in a frequency characteristic of vibration of liquid 50. According to this configuration, drive frequency f1 is set to a frequency closer to resonance frequency fr1 of liquid 50. Therefore, the amplitude of the mechanical vibration of liquid 50 further increases, and discharge can be more stably generated.

In voltage application device 1, 1A in a fifth aspect, in any of the first to fourth aspects, voltage application circuit 2 is configured in such a way that drive frequency f1 can be changed within predetermined range W1.

According to this configuration, for example, in a case where discharge does not stably occur, drive frequency f1 is changed to become closer to resonance frequency fr1 of liquid 50, so that discharge can be more stably generated.

In voltage application device 1, 1A in a sixth aspect, in any of the first to fifth aspects, the applied voltage is adjusted as described below in such a way that a generation amount of ozone per unit time resulting from discharge generated in discharge electrode 41 during the drive period is less than or equal to a specified value. Stated another way, maximum value V2 of the applied voltage during the drive period is adjusted to be less than or equal to a specified voltage value.

According to this configuration, an increase in a generation amount of ozone per unit time resulting from an increase in drive frequency f1 can be suppressed.

In voltage application device 1, 1A in a seventh aspect, in any of the first to sixth aspects, a volume of liquid 50 is adjusted as described below in such a way that a generation amount of ozone per unit time resulting from discharge generated in discharge electrode 41 during the drive period is less than or equal to a specified value. Stated another way, the volume of liquid 50 during the drive period is adjusted to be greater than or equal to a specified volume.

According to this configuration, an increase in a generation amount of ozone per unit time resulting from an increase in drive frequency f1 can be suppressed.

Discharge device 10, 10A in an eighth aspect includes voltage application device 1, 1A in any of the first to seventh aspects and discharge electrode 41.

According to this configuration, liquid 50 mechanically vibrates at drive frequency f1 near resonance frequency fr1 of liquid 50 to vibrate at a relatively large amplitude. Therefore, when an electric field acts on liquid 50, the distal end has a more sharply pointed shape. Accordingly, in liquid 50, a field intensity required for dielectric breakdown is reduced, and discharge more easily occurs, in comparison with a case where liquid 50 mechanically vibrates at a frequency away from resonance frequency fr1 of liquid 50. Therefore, for example, even when there is a variation in a magnitude of a voltage applied from voltage application circuit 2 to load 4, a variation in a shape of discharge electrode 41, a variation in an amount of liquid 50 supplied to discharge electrode 41, or another variation, discharge can stably occur. As a result, there is an advantage by which discharge device 10, 10A can more stably generate discharge.

In the eighth aspect, discharge device 10, 10A in a ninth aspect further includes liquid supply unit 5 that supplies liquid 50 to discharge electrode 41. According to this configuration, liquid 50 is automatically supplied to discharge electrode 41 by liquid supply unit 5. Therefore, a task of supplying liquid 50 to discharge electrode 41 is omitted.

In the ninth aspect, discharge device 10, 10A in a tenth aspect further includes sensor 7 that measures at least one of a temperature and a humidity. Liquid supply unit 5 is configured to cool down discharge electrode 41 and generate dew condensation water serving as liquid 50 on a surface of discharge electrode 41.

According to this configuration, sensor 7 can measure at least one of a temperature and a humidity that affect a generation amount of liquid 50 in a configuration in which liquid supply unit 5 condenses moisture in the air, and supplies dew condensation water serving as liquid 50. Therefore, a generation amount of liquid 50 in liquid supply unit 5 can be obtained, for example, on the basis of an output of sensor 7.

In the tenth aspect, discharge device 10, 10A in an eleventh aspect further includes adjuster 8 serving as a frequency adjuster that adjusts drive frequency f1 on the basis of the output of sensor 7.

According to this configuration, drive frequency f1 is adjusted on the basis of at least one of a temperature and a humidity. Therefore, even when resonance frequency fr1 of liquid 50 changes according to temperature or humidity, drive frequency f1 can be caused to be closer to resonance frequency fr1.

In the tenth or eleventh aspect, discharge device 10, 10A in a twelfth aspect further includes adjuster 8 serving as a generation amount adjuster that adjusts a generation amount of dew condensation water in liquid supply unit 5 on the basis of the output of sensor 7.

According to this configuration, the generation amount of liquid 50 in liquid supply unit 5 is adjusted on the basis of at least one of a temperature and a humidity. Therefore, even when resonance frequency fr1 of liquid 50 changes according to temperature or humidity, drive frequency f1 can be caused to be closer to resonance frequency fr1.

In any of the eighth to twelfth aspects, discharge device 10, 10A in a thirteenth aspect further includes counter electrode 42 that is disposed to face discharge electrode 41 via a gap. Discharge device 10, 10A is configured to generate discharge between discharge electrode 41 and counter electrode 42 due to application of voltage between discharge electrode 41 and counter electrode 42.

According to this configuration, a discharge path through which a discharge current flows after dielectric breakdown can be stably generated between discharge electrode 41 and counter electrode 42.

In discharge device 10, 10A in a fourteenth aspect, in any of the eighth to thirteenth aspects, liquid 50 is electrostatically atomized due to discharge.

According to this configuration, charged fine particle liquid containing radicals is generated. Accordingly, the lifetime of radicals can be prolonged in comparison with a case where radicals are emitted as a simple substance into the air. Further, the charged fine particle liquid has, for example, a nanometer-size, so that the charged fine particle liquid can float within a relatively wide range.

The configurations in the second to seventh aspects are not an essential configuration in voltage application device 1, 1A, and can be appropriately omitted. The configurations in the ninth to fourteenth aspects are not an essential configuration in discharge device 10, 10A, and can be appropriately omitted.

INDUSTRIAL APPLICABILITY

A voltage application device and a discharge device can be applied to various purposes such as refrigerators, washing

REFERENCE MARKS IN THE DRAWINGS 1, 1A: voltage application device
2: voltage application circuit
4: load
5: liquid supply unit
7: sensor
8: adjuster
10, 10A: discharge device
41: discharge electrode
42: counter electrode
50: liquid (dew condensation water)
f1: drive frequency
fr1: resonance frequency
V2: maximum value
V0: minimum value
W1: predetermined range

The invention claimed is:

1. A voltage application device comprising:
a voltage application circuit that applies a voltage to a load including a discharge electrode that holds liquid, the voltage application circuit generating discharge in the discharge electrode; and
a control circuit configured to control the voltage application circuit,
wherein, during a drive period, the voltage application circuit periodically changes a magnitude of the voltage applied to the load at a drive frequency within a predetermined range including a resonance frequency of the liquid, the voltage application circuit mechanically vibrating the liquid,
the load includes a counter electrode that is disposed to face the discharge electrode via a gap,
the voltage is applied between the discharge electrode and the counter electrode, such that dielectric breakdown is generated between the discharge electrode and the counter electrode,
the control circuit is configured to periodically perform
(i) monitoring the output voltage of the voltage application circuit, and reducing energy input to the voltage application circuit, when the output voltage becomes greater than or equal to a maximum value and the dielectric breakdown is generated,
(ii) monitoring an output current of the voltage application circuit after the dielectric breakdown occurs, and reducing energy input to the voltage application circuit, when the output current is greater than or equal to a threshold, such that the dielectric breakdown occurs intermittently in accordance with the drive frequency,
during the drive period, the magnitude of the voltage changes within a range and the magnitude is greater than 0 V within the range,
the liquid includes dew condensation water that is located on a surface of the discharge electrode, and
the voltage application device further includes an adjuster that is configured to adjust a generation amount of the dew condensation water based on at least one of a temperature and a humidity.

2. The voltage application device according to claim 1, wherein a differential value between a maximum value and a minimum value of the voltage during the drive period is greater than or equal to 1/2 of the maximum value of the voltage.

3. The voltage application device according to claim 1, wherein the predetermined range is a range of full width at half maximum (FWHM) in a frequency characteristic of vibration of the liquid.

4. The voltage application device according to claim 1, wherein the voltage application circuit changes the drive frequency within the predetermined range.

5. The voltage application device according to claim 1, wherein a maximum value of the voltage during the drive period is adjusted to be less than or equal to a specified voltage value in such a way that a generation amount of ozone per unit time resulting from the discharge generated in the discharge electrode during the drive period is less than or equal to a specified value.

6. The voltage application device according to claim 1, wherein a volume of the liquid during the drive period is adjusted to be greater than or equal to a specified volume in such a way that a generation amount of ozone per unit time resulting from the discharge generated in the discharge electrode during the drive period is less than or equal to a specified value.

7. A discharge device comprising:
the voltage application device according to claim 1.

8. The discharge device according to claim 7, further comprising a liquid supply unit that supplies the liquid to the discharge electrode.

9. The discharge device according to claim 8, further comprising a sensor that measures the at least one of the temperature and the humidity,
wherein the liquid supply unit cools down the discharge electrode, and generates dew condensation water serving as the liquid on the surface of the discharge electrode.

10. The discharge device according to claim 9, wherein the adjuster is further configured to adjust the drive frequency based on an output of the sensor.

11. The discharge device according to claim 7, wherein the liquid is electrostatically atomized due to the discharge.

12. The voltage application device according to claim 1, wherein, during the drive period, the magnitude of the voltage is always greater than 0 V within the range.

* * * * *